Nov. 6, 1962 E. B. LE GRICE Plant Pat. 2,190
HYBRID TEA-ROSE PLANT
Filed May 2, 1961
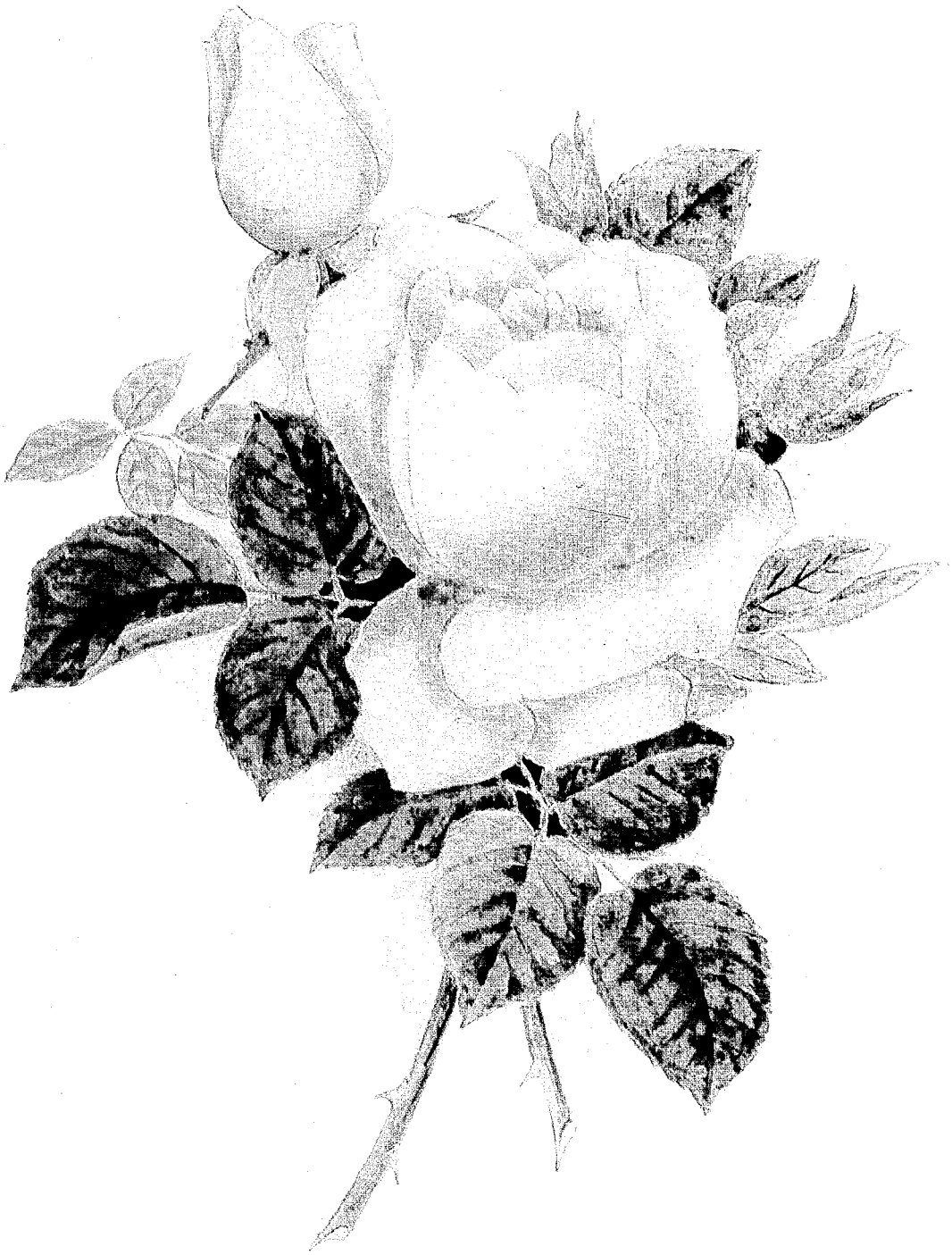
WITNESS
Addison E. Avery
INVENTOR
Edward Burton Le Grice,
by: John H. Leonard,
his ATTY.

United States Patent Office

Plant Pat. 2,190
Patented Nov. 6, 1962

2,190
HYBRID TEA-ROSE PLANT

Edward Burton Le Grice, North Walsham, Norfolk, England

Filed May 2, 1961, Ser. No. 107,277
1 Claim. (Cl. 47—61)

This invention relates to a new variety of rose plant which is a hybrid tea rose.

The present rose plant was produced originally by the crossing of Wellworth, unpatented, as a seed parent, and Independence, Plant Patent No. 1,036, as the pollen parent.

The new variety was crossed intentionally in my hybridizing greenhouse in North Walsham, England, in 1955.

The new variety was asexually reproduced by me in 1956 at North Walsham, England, by budding. The new variety was tested by the National Rose Trial Grounds, St. Albans, England, in January 1959.

The drawing shows in color a number of typical stalks with leaves, buds, blooms and thorns.

The exposed portion of the plant is in the form of a hardy, perennial, woody bush which is upright, bushy, symmetrical in shape, and peaked at the top. It grows generally to a height of about 2½ feet and has a spread of about 2 feet. It is a medium grower.

The exposed portion of the plant has good resistance to low temperatures when protected and fair resistance when unprotected. Its resistance to drought is good.

For growth, the new variety prefers moderate sun or partial shade, with a south, southwest, or west exposure and thrives in well drained, rich loam soil.

The main stalks of the plant are upright, slightly branched and stiff. They are adequate to support the foliage and blooms well.

The following color designations are from the British Color Council Horticultural Color Chart and are designated by sheet and number.

The new growth of the stalks are Chrysanthemum Crimson, No. 824/3 and mottled. The joints above the leaf bud are Lettuce Green, No. 861/3. The old growth is Spinach Green, Sheet 187, No. 0960/3. The color is uniform.

The main stalks range from about 12 to 18 inches in length and are divergent. They have a prickly surface texture, smooth and glossy between thorns. The branches are alternate and prickly, abundant and stiff. They are long and straight and adequate to support the foliage well.

The foliage in general is normal, the leaf arrangement being opposite. The leaves are average in quantity. The new leaves are a uniform Pansy Purple, Sheet 177, No. 928/3, on the top and on the bottom surfaces are Indian Lake, Sheet 170, No. 826/3. The old leaves are uniform in color and are Spinach Green, Sheet 187, No. 0960/3, on the top and Willow Green, Sheet 199, No. 000862, on the bottom.

The red foliage in the young state is like that of Independence (Plant Patent No. 1,036).

The leaves are of medium size, ranging from 4 inches average to 5 inches maximum in length and have a minimum width of 2½ inches. They are of the usual shape, being imparipinnate with serrated margins, sagittate bases, and acute apices. They are of average thickness. They are smooth and slightly glossy on the upper face and smooth and dull on the reverse. Their persistency on the plant is good and their leaf characteristics are usual.

The petioles or leaf stems are of the same color pattern as the old and young wood. They are average in length, being about 1 inch, and strong. They have a smooth surface texture.

The stipules are pronounced and slightly fimbriated.

The plant grows and blooms well in all temperate regions. It prefers sun, southern or western exposures, dry cold seasons, and a well drained moist, rich loam soil of about pH 6.5. Changes in exposure, wetness, coldness of season and quality of soil do not cause much variation in the quality of the blooms. They open well in all weather. Their quantity varies with the type of soil.

The plant blooms well under all conditions and the color of the blooms fades when very hot. The blooming is recurrent for a period of about five months. The flowers remain in good condition for a long period when cut. The uncut flowers change color upon opening. They are strong. The blooms open slowly, their rate of opening increasing with hot sun.

The buds are average, being medium in size and pear-shaped. They are smooth and supported upright in clusters on terminals and laterals.

When the sepals first divide, the petal color is Indian Lake, Sheet 170, No. 826/3. When they begin to unfurl, the color is Rose Madder, Sheet 23, No. 23. When half blown, the color is Carmine, Sheet 21, No. 21.

The sepals are of the normal shape and size.

The calyx is of normal shape, being about ¾ of an inch in size, with a smooth outer side and with the inner side downy.

The peduncles average from 2 to 3 inches in length. They are smooth and their color is Pea Green, No. 61/1. They are strong.

The peduncles average from 2 to 3 inches in length. Their texture is smooth and the color generally is Pea Green, No. 61/1, shaded slightly with Crimson, No. 22.

The blooms average from 4 inches in diameter to 5 inches and an average plant will bear from 30 to 35 blooms at the same time. The blooms are borne singly. Each flower lasts from 3 to 5 days both when cut and uncut.

Each bloom has from 25 to 30 petals and is generally Carmine, Sheet 21, No. 21/2. The petals at the center of the bloom are Carmine, Sheet 21, No. 21/2. The outer petals and the base of the petals are Carmine, Sheet 21, No. 21. The inside of the petals is a uniform Carmine, Sheet 21, No. 21/2, and the reverse of the petals ranges from Carmine, Sheet 21, No. 21 to Scarlet, Sheet 19, No. 19.

The general tonality of the plant from a distance, when it is in bloom, is Carmine ranging from deep to light Carmine, growing lighter gradually after blooming.

The petals are very thick and waxy and are satiny on the inside and dull on the outside. They are recurvent. The arrangement of the petals is the usual even outline. There are from 2 to 3 petaloids in the center and their persistence is good when cut or uncut. The bloom is of the usual shape.

The fragrance of the blooms is a medium perfume. Its lasting quality is good when the blooms are cut or uncut.

The stamens are normal and Lemon, No. 4/1. The filaments are medium and in color Scarlet, No. 19/2. The pollen is Lemon Yellow, No. 4.

The styles are about ¼ of an inch in length and are Scarlet, No. 4/1, at the top and Lemon, No. 4/3, at the base. The stigmas are about 1/16 of an inch in length and their color is Lemon, No. 4/3. The ovaries are plentiful.

There are moderate thorns on the main stalk from the base of the plant. On the laterals there are few. The thorns are short, stiff, and wedge shaped. Their color is Chrysanthemum Crimson, No. 824/3. They are evenly distributed on the main stalk and on the laterals, and sparse on the peduncles.

The drawing further illustrates the characteristics of the variety and the following tabulation is a detailed description of the new variety;

*General*

Parentage:

*Seed parent.*—Wellworth. Wellworth is from Leontine Continot and Golden Dawn. It is an unpatented hybrid tea rose listed on page 850, Roses, 1958, National Rose Society of Great Britain.

*Pollen parent.*—Independence, Plant Patent No. 1,036.

Classification: Botanic—Rosa, hybrid tea.

Blooming habit: Location where observations were made: North Walsham, England; Brundall, Norwich, England; National Rose Trial Grounds, St. Albans, England.

Bud:

*Size.*—Medium.

*Form.*—Pear-shaped.

*Color.*—When petals first divide, their color is Indian Lake, Sheet 170, No. 826/3. When they begin to unfurl, they are Rose Madder, Sheet 23, No. 23. When half blown, they are Carmine, Sheet 21, No. 21.

*Sepals.*—Normal shape and size.

*Calyx.*—Of the normal shape, about ¾ of an inch in size with a smooth outer side and with the inner side downy.

*Peduncle.*—Length—from 2 to 3 inches. Aspect—smooth. Color—Pea Green, No. 61/1.

*Pedicles.*—Length — 2 to 3 inches. Texture — smooth. Color—Pea Green, No. 61/1, shaded slightly Crimson, No. 22.

*Opening.*—Slow—more quickly in hot sun.

Bloom:

*Size.*—4 to 5 inches in diameter. Average bloom per plant—30 to 35.

*Borne.*—Singly.

*Stems.*—Length—about 1 inch; strong. Aspect—smooth.

*Form.*—Large proportion borne singly.

*Permanence.*—3 to 5 days, cut and uncut.

Petalage:

*Texture.*—Thick and waxy.

*Appearance.*—Satiny on the inside and dull on the outside.

*Form.*—Usual.

*Arrangement.*—Usual even outline.

*Petaloids.*—2 to 3.

*Persistence.*—Good when cut and uncut.

*Fragrance.*—Medium perfume.

*Lasting quality.*—Good when cut or uncut.

Genital organs:

*Stamens.*—Normal. Color—Lemon, No. 4/1.

*Filaments.*—Medium, color Scarlet, Sheet 19, No. 19/2.

*Pollen.*—Lemon Yellow, No. 4

*Styles.*—½ inch, color—top Scarlet, No. 4/1; base Lemon, No. 4/3.

*Stigmas.*—1/16 of an inch, color Lemon No. 4/3.

*Ovaries.*—Plentiful.

*Plant*

Form: A hardy perennial woody bush, upright, bushy and symmetrical in shape and peaked at top.

Growth: Medium. Height about 2½ feet with spread of 2 feet.

Leaves: Normal.

*Size.*—4 to 5 inches in length and minimum width of 2½ inches.

*Quantity.*—Average.

*Color.*—New leaves on top—Pansy Purple, Sheet 177, No. 928/3. New leaves on bottom—Indian Lake, Sheet 170, No. 826/3. Old leaves on top—Spinach Green, Sheet 187, No. 0960/3. Old leaves on bottom—Willow Green, Sheet 199, No. 000862. Red foliage in young state like that of Independence, Plant Patent No. 1,036.

*Shape.*—Imparipinnate with serrated margins, sagittate bases, and acute apices.

*Texture.*—Upper surface — smooth and slightly glossy. Lower face—smooth and dull.

*Persistency.*—Good.

*Leaf characteristics.*—Usual.

Petiole: Length—about 1 inch with a smooth surface texture. Strong. Color same as old and new wood.

Stipules: Pronounced and slightly fimbriated.

Wood:

*Newest wood.* — Chrysanthemum Crimson, No. 824/3.

*Bark.*—Prickly.

*Old wood.*—Spinach Green, Sheet 187, No. 0960/3.

Thorns:

*Quantity.*—On main stalks, moderate. Laterals, few.

*Form.*—Wedge shaped.

*Color.*—Chrysanthemum Crimson, No. 824/3.

*Position.*—Evenly distributed on the main stalk and laterals and few on the peduncles.

The plant is characterized particularly by well formed blooms of a consistent color, useful for forcing as well as bedding outside. A noteworthy feature is the slow early development of the flower bud at the end of the shoot. This is followed by rapid development in the second period. A large proportion of the flowers come singly. The most unusual features are the strength of the laterals, each developing a good flower stem, and the endurance of the red of the foliage which remains until full bud development.

Having shown and described my new variety of hybrid tea rose plant and its manner of asexual reproduction, I claim:

The new and distinct variety of hybrid tea rose plant herein shown and described.

No references cited.